United States Patent [19]

Chiu et al.

[11] Patent Number: 4,910,337

[45] Date of Patent: Mar. 20, 1990

[54] PROCESS FOR THE PREPARATION OF α-ARYLALKANOIC ACIDS

[75] Inventors: Kuen-Wai Chiu, Wexford; Mary H. Staruch, Butler; David H. Ellenberger, Chicora, all of Pa.

[73] Assignee: Mine Safety Appliances Company, Pittsburgh, Pa.

[21] Appl. No.: 302,250

[22] Filed: Jan. 27, 1989

[51] Int. Cl.$^4$ .............................................. C07C 57/30
[52] U.S. Cl. ................................... 562/496; 562/460; 562/462; 562/490
[58] Field of Search ............... 562/496, 460, 462, 490

[56] References Cited

U.S. PATENT DOCUMENTS 3,600,437  8/1971  Marshall ............................. 562/465

FOREIGN PATENT DOCUMENTS 971700  9/1964  United Kingdom .

OTHER PUBLICATIONS

Lochmann, L. et al., Collection Czechoslovak Chem., Comm. [vol. 51], 1986.

L. Lochmann, First and Second Generation of Superbases from Organolithium Compounds and Heavier Alkali Metal Alkoxides, 196th ACS National Meeting, Sep. 25–30, 1988.

Primary Examiner—Paul J. Killos

[57] ABSTRACT

α-Arylalkanoic acids are prepared by a method comprising the step of reacting an alkylaromatic compound corresponding to the desired α-arylalkanoic acid with a new metallation reagent solution. The reagent comprises the reaction product of alkyllithium or aryllithium and about two to five molar equivalents of potassium tert-alkoxide in a trialkylamine solvent.

6 Claims, No Drawings

PROCESS FOR THE PREPARATION OF α-ARYLALKANOIC ACIDS

FIELD OF THE INVENTION

This invention relates to a novel strong base reagent useful in metallation and coupling addition, elimination and polymerization reactions and a process for the preparation of α-arylalkanoic acids. More particularly, this invention relates to novel processes for preparing an aromatic alkanoic acid starting from an alkylbenzene or alkylbenzene derivative utilizing a novel alkyl or aryllithium-potassium tertiary-alkoxide complex-aggregate in a trialkylamine solvents.

BACKGROUND OF THE INVENTION

The compounds prepared by the process of this invention are α-arylalkanoic acid derivatives of the general formula

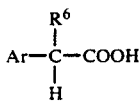

and are characterized by having an aryl and an alkyl group at the α-position. In the formula, Ar represents an aryl of 6–13 carbon atoms and is an optionally substituted phenyl, phenoxyphenyl, naphthyl, biphenyl group or amino-substituted phenyl group; $R^6$ is hydrogen or $C_{1-4}$ alkyl group.

For almost a century, aspirin has dominated as a mild anti-inflammatory, analgesic and antipyretic agent. Over the last twenty years there has been great demand for aspirin-like drugs having higher therapeutic response and less side effects than aspirin itself. α-Arylalkanoic acids, particularly the α-arylpropionic acids, have already proven to be suitable compounds to fulfill these requirements. In fact, some of them, like Fenoprofen, Naproxen (S) and Ibuprofen have already been extensively used in medical practice. Their therapeutic effects were related to the inhibition of prostaglandin biosynthesis. These compounds have valuable anti-inflammatory, analgesic and antipyretic properties. Clinical efficacy has been demonstrated in rheumatoid arthritis and osteoarthritis. Furthermore, in general, the compounds exhibit low toxicity and low irritancy to the gastric mucosa; they do not have other undesirable pharmacological activities which might give rise to unwanted side effects. Hence, the need has arisen for new and improved, economical synthetic procedures suitable for their preparation and manufacture on an industrial scale.

Conventional methods for producing these pharmaceuticals are complicated and industrially disadvantageous. Typical reported methods for producing Fenoprofen [2-(3-phenoxyphenyl)propionic acid] are:

(1) The method of U.S. Pat. No. 3,600,437 which comprises sodium borohydride reduction of m-phenoxyacetophenone to α-(m-phenoxyphenyl)-ethyl alcohol, reaction with phosphorus tribromide to form α-(m-phenoxyphenyl)ethyl bromide, displacement of the bromine with sodium cyanide in dimethyl sulfoxide, followed by hydrolysis with sodium hydroxide to furnish the desired α-(m-phenoxyphenyl)propionic acid. This method is disadvantageous in that the product is prepared in a multi-step synthesis which involves the use of m-phenoxyacetophenone as a starting material, which in turn is obtained from m-hydroxyacetophenone via the coupling reaction with bromobenzene catalyzed by a copper catalyst. Due to the meta-orientation of the hydroxy group, m-hydroxyacetophenone cannot be obtained directly by simple procedures and is expensive. The m-phenoxy-2-phenethylbromide intermediate is unstable and creates problems in mass production. Moreover, the process necessitates the use of sodium cyanide which is extremely poisonous and undesirable from a safety viewpoint.

(2) The method of Japanese Pat. No. 45586/76 CA 75:48707m (1971) which comprises bromination of m-methyl diphenyl ether with N-bromosuccinimide to form m-(bromomethyl)diphenyl ether, displacement of the bromine with sodium cyanide in dimethylsulfoxide to form m-(cyanomethyl)diphenyl ether, hydrolysis followed by esterification to give ethyl α-(m-phenoxyphenyl)acetate, conversion to form diethyl 2-(m-phenoxyphenyl)malonate by reacting the ester with diethyl carbonate and sodium, methylation with methyl iodide to furnish diethyl 2-methyl-2-(m-phenoxyphenyl)malonate, and finally, hydrolysis followed by decarboxylation to obtain the product α-(m-phenoxyphenyl)propionic acid.

This method is also laborious, involving the introduction and removal of a carboxyl group, the use of N-bromosuccinimide, an expensive reagent, and also the use of the poisonous cyanide reagent.

Conventional reported methods for producing Ibuprofen [2-(4-isobutylphenyl)propionic acid] are:

(1) The method of British Pat. No. 971,700/64 and Japanese Pat. No. 7491/65 which comprises the conversion of a p-isobutylphenylacetic acid ester by the action of dialkyl carbonate in the presence of a base to form the corresponding malonic ester, methylation of the malonic ester with methyl iodide, hydrolysis and subsequent removal of the carboxyl group through pyrolysis to afford the desired propionic acid.

(2) The method of Japanese Pat. No. 18105/72 which comprises the reaction of p-isobutylacetophenone with potassium cyanide and ammonium carbonate to form the corresponding hydantoin, hydrolysis of the hydantoin to obtain an α-amino acid, alkylation to give dialkylamino product, and finally hydrogenation to furnish 2-(4-isobutylphenyl)-propionic acid.

(3) The method of Japanese Pat. No. 24550/72 CA 72:21492p (1970) which comprises the reaction of p-isobutylacetophenone with a monochloroacetic acid ester under the Darzen reaction conditions to obtain the corresponding epoxycarboxylic acid ester, hydrolysis and decarboxylation to afford α-(p-isobutylphenyl)propionaldehyde, and then oxidation to give the desired propionic acid.

(4) The method of European Pat. No. 34871/81; CA 96(5):34940d (1981) which comprises the rearrangement of alpha-haloketals of p-isobutylacetophenone in the presence of a Lewis acid.

These methods are industrially disadvantageous in that they involve multi-step reactions and all start from isobutylacetophenone which is prepared through acylation of isobutylbenzene under Friedel-Crafts reaction conditions with aluminum chloride. The mass amount of aluminum hydroxide formed during a normal workup usually creates an isolation problem for the product and, furthermore, it imposes a waste disposal problem.

SUMMARY OF THE INVENTION

An object of this invention is to provide an improved strong base reagent solution for organic reactions comprising the reaction product of a molar equivalent of an alkyllithium or aryllithium with two to five molar equivalents of a potassium tertiary-alkoxide in a trialkylamine solvent. The reagent is useful in metallation, coupling, elimination, addition and polymerization reactions. The reagent is believed to be a solvated complex of alkylpotassium or arylpotassium with potassium alkoxide and with or without lithium alkoxide.

More particularly the reagent is a solution of the reaction product of $$R^1Li,$$

where $R^1$ is a $C_{1-10}$ alkyl group, a phenyl group, a lower alkoxyphenyl or dialkoxyphenyl group in which the alkoxy group has 1 to 4 carbon atoms, or an aryloxyphenyl group, such as, for example, phenyloxyphenyl, and between about two and five molar equivalents of $$KOR^2,$$

wherein $R^2$ is a tert-alkyl group having 4 to 7 carbon atoms, such as, for example, tert-butyl, tert-amyl, 2,3-dimethyl-2-butanyl, 2-methyl-2-pentanyl, 3-methyl-3-pentanyl, 3-ethyl-3-pentanyl, 2,3-dimethyl-3-pentanyl, 2-methyl-2-hexanyl
in a trialkylamine medium comprising one or more trialkylamines of the formula $$NR^3R^4R^5,$$

wherein $R^3$, $R^4$ and $R^5$ are each a $C_{1-18}$ alkyl group or $R^3$ and $R^4$ form together an α, ω-alkylene group containing from 1 to 8 carbon atoms.

A further object of this invention is to provide a novel process for preparing in high yield and high selectivity an arylalkanoic acid by reaction of the aforesaid strong base reagent with an alkylaromatic compound of the formula $$Ar-CH_2-R^6$$

followed by carbonation and acidification of the resulting reaction mixture wherein Ar is a substituted or unsubstituted aromatic group and $R^6$ is a $C_{1-4}$ alkyl group of hydrogen atom.

DETAILED DESCRIPTION OF THE INVENTION AND PREFERRED EMBODIMENTS

The arylalkanoic acids prepared by the method of the invention are represented by the formula

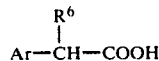

in which $R^6$ is a $C_{1-4}$ alkyl group or hydrogen atom and Ar is a substituted or unsubstituted aromatic group of the formula

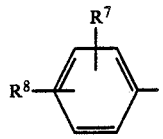

wherein $R^7$ and $R^8$ may be the same or different and each represents a hydrogen atom, an alkyl group, an aryl group, an $OR^9$ group in which $R^9$ represents a hydrogen atom, an alkyl group, an aryl group, or a protected $O=C-R^{10}$ group in which $R^{10}$ represents an alkyl or aryl group; or a group of the formula:

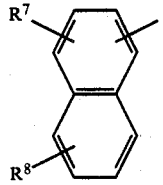

Ar preferentially represents 3-phenoxyphenyl, 4-isobutylphenyl, 6-methoxynaphth-2-yl, 2-methylnaphth-1-yl, 4-biphenyl, or 3-benzoylphenyl.

The metallation reagent is contacted and reacted with an alkylaromatic compound

in which Ar and $R^6$ correspond to the desired Ar and $R^6$ groups in the arylalkanoic acid, to form an arylalkyl potassium derivative

which is conventionally carbonated and acidified to form the arylal-kanoic acid.

Preparation of the Reagent

Since the metallation reagent comprises the reaction product of aryllithium or alkyllithium with potassium tertiary-alkoxide, hereafter generally referred to as the complex-aggregate, the choice of the aprotic solvents which have both proper stability and polarity toward this complex-aggregate is important. Most of the common solvents like tetrahydrofuran, diethyl ether, the glymes, dimethylsulfoxide, dimethylformamide, acetonitrile, are decomposed by the complex-aggregate. The reactive n-butyllithium-potassium tertiary-butoxide complex-aggregate is stable in most saturated hydrocarbons; however, the complex-aggregate lacks solubility in most of these solvents so the reactivity of the reagent is greatly reduced. It is essential that the solvent medium is a trialkylamine, such as triethylamine and the like, and most preferably cyclic trialkylamine such as N-methylpyrrolidine, N-methylpiperidine and the like or a mixture of the above aforementioned amines. The cyclic amines provide an additional advantage of being able to coordinate like tetrahydrofuran with the organometallic reagents and thus enhance the stability, solubility and reactivity of the organometallic species in the reaction medium.

It is essential in this reagent that the potassium tertiaryalkoxide is used in an amount of not less than two times, preferably four to five times in molar equivalent with respect to the alkyllithium. This suggests that the actual reaction species of the reagent is not an alkyl or aryl potassium but is the alkyl or aryl potassium-potassium alkoxide complexes with up to three alkoxide ligands of the formula $R^1K_4(OR^2)_3 \cdot X$ Solvent or $R^1K_4Li(OR^2)_4 \cdot X$ Solvent The exchange reaction of one molar equivalent of potassium tertiary-alkoxide with one molar equivalent of alkyllithium is known to form alkylpotassium compounds or alkyllithium-potassium tertiary-alkoxide 1:1 adducts that are useful in metallation, coupling, elimination, addition and polymerization reactions. These alkylpotassium compounds or 1:1 adducts have been used in diethyl ether, tetrahydrofuran or hydrocarbon media, resulting in heterogeneous reaction systems. Furthermore in polar solvents like tetrahydrofuran and diethyl ether, reactions have to be operated below $-40°$ to $-50°$ to avoid decompositions of these alkylpotassium compounds. See, for example, L. Lochmann, J. Pospisil and D. Lim, *Tetrahedron Lett.* 1966, 257; L. Lochmann and D. Lim, *J. Organomet. Chem.* 1971, 28, 153; and M. Schlosser and S. Strunk, *Tetrahedron Lett.* 1984, 741.

The new strong base reagents of this invention comprise a homogeneous solution of complex-aggregate and are much stronger metallating agents than the above described alkylpotassium compounds; significantly, it is a much more stable system which enables reactions to be run at temperatures $\geq 0°$ C.

In the preparation of the new reagent, the first molar equivalent of potassium tertiary-alkoxide is believed consumed in the generation of the alkylpotassium from the corresponding alkyllithium, and the additional potassium tertiary-alkoxide forms complex-aggregate. Due to the polarization of the carbon-potassium bond by the alkoxide ligands, these organopotassium complexes exhibit superb solubility and metallation power when prepared in the aforementioned amine solvent-systems.

The reagent is preferably freshly prepared for use and in many instances it is convenient and desirable to form the reagent in situ in the presence of the substrate to be metallated.

The complex-aggregate is effective in metallating compounds not readily metallated by prior methods. For example, an arylethane can be metallated and converted to the corresponding pharmaceutically valuable arylpropionic acid (upon carbonation and acidification) in one step without relying on the further methylation reaction on the arylacetic acid-ester with methyl iodide or dimethyl sulfate as described above. (The arylacetic acid analogues without the α-methyl substituent have been abandoned from use because they had been found to show skin and liver toxicity in man.)

Another advantage of the new complex-aggregate reagent is that it provides very selective reaction toward certain meta- and para-substituted arylalkanes. For example, in the preparation of Fenoprofen, [2-(3-phenoxyphenyl)propionic acid] starting from 85% pure 3-phenoxyphenylethane containing 15% 4-phenoxyphenylethane, 2-(3-phenoxyphenyl)propionic acid formed exclusively. This unique selectivity permits the use of the very inexpensive technical grade 3-ethylphenol (containing approximately 10% of the 4-ethylphenol isomer) as the starting material. The pure 3-ethylphenol which can be obtained by chemical separation is costly. The yield of phenoxyphenylethane made from the technical grade 3-ethylphenol is over 90% via the coupling reaction with bromobenzene catalyzed by a complex copper catalyst.

Preparation of α-Arylalkanoic Acids

From the viewpoint of reaction mechanism, in many cases, the main reaction routes for obtaining the arylalkanoic acids from the arylalkane are believed to proceed through either of the following two reaction schemes, depending on whether an aryl ether is used. The reaction scheme without aryl ether proceeds by the metallation of a benzene nucleus proton by the complex-aggregate to form an aryl anion, the transmetallation reaction on an α-methylene proton of an arylalkane by an aryl anion to give a benzyl potassium derivative, and the carbonation of the thus formed benzyl potassium derivative to give an arylalkanoic acid upon acidification. The preparation of Fenoprofen, 2-(3-phenoxyphenyl)-propionic acid, is used as an illustrative example.

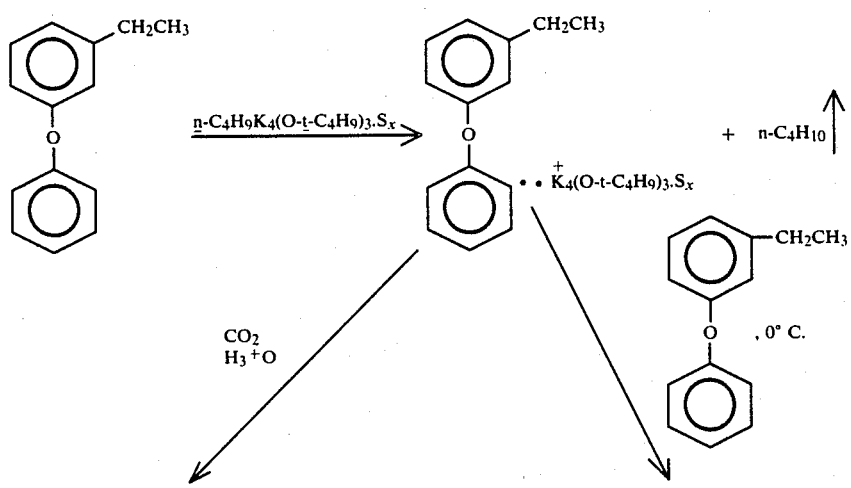

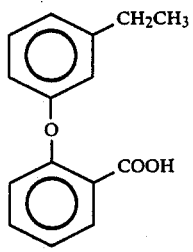

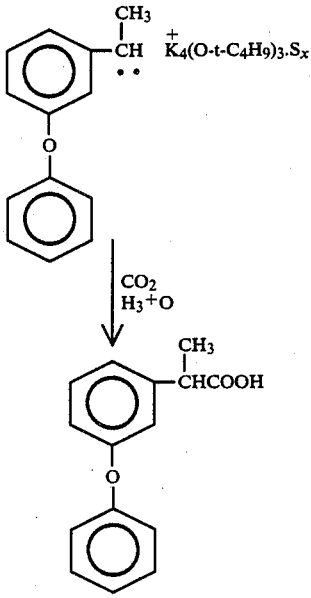

The reaction is believed to proceed in a different fashion with an introduction of an equimolar quantity of an aryl ether of the formula Ar—O—R$^{11}$ in which R$^{11}$ is a C$_{1-4}$ alkyl group or an Ar group and Ar is a substituted or unsubstituted aromatic group of the formula

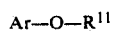

wherein R$^7$ and R$^8$ may be the same or different and each represents a hydrogen atom, an alkyl group, an aryl group, an OR$^9$ group in which R$^9$ represents an alkyl group or an aryl group; or a group of the formula:

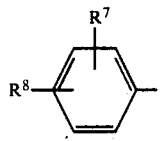

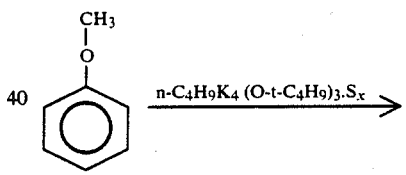

With such ethers, as, for example, anisole, phenyl ether, butyl phenyl ether, dimethoxybenzene, methoxybiphenyl, dimethoxybiphenyl, methoxynaphthalene, dimethoxynaphthalene, or 1,2-diphenoxyethane the reaction proceeds via the metallation of a benzene nucleus proton of an aryl ether by the complex-aggregate to form an aryl anion, the transmetallation reaction on an α-methylene proton of an aryl alkane by the thus formed aryl anion to obtain a benzyl potassium derivative, and the carbonation with dry-ice and acidification.

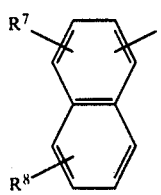

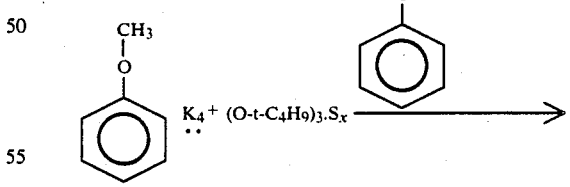

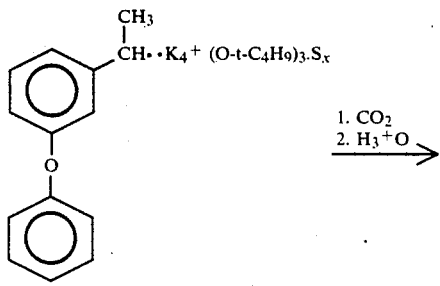

-continued

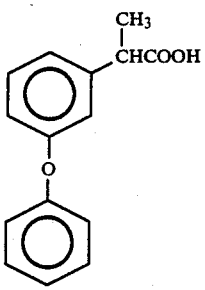

It is an advantage in this reaction that the potassium cation exhibits the unique properties in stabilizing the delocalized benzyl anion which upon carbonation and acidification furnishes the desired arylalkanoic acid. Whereas, the similar reaction using sodium tertiary-alkoxide fails to give the desired product at the same time and temperatures, but instead, the corresponding benzoic acid was obtained predominantly.

The temperature control in this invention is not very critical. At low temperature (below −30° C.), the aryl anion did not transmetallate to form the benzyl anion and ended up to form benzoic acids upon carbonation and acidification. Usually, the aryl anion transmetallates well above −25° C. and temperatures up to at least about +25° C. can be used.

The following are examples of preferred methods and comparative examples demonstrating the benefits of the complex-aggregate metallation reagent.

EXAMPLE 1

To a mixed solvent of dried 1-methylpyrrolidine (6.0 ml.) and triethylamine (10.0 ml.) were added potassium tertiary-butoxide (17.5 g., 167 mmoles), an isomeric mixture of 3- and 4-ethylbiphenyl ether (6.50 g., 32.8 mmoles) containing 85% pure 3-ethylbiphenyl ether (5.53 g., 27.9 mmoles), and then anisole (3.00 g., 27.8 mmoles) with cooling at 0° C. with stirring under a nitrogen atmosphere for 15 minutes. n-Butyllithium (2.50M) (12.0 ml., 30.0 mmoles) was added dropwise to the reaction mixture over a period of 10 minutes. After completion of the addition, the mixture was stirred for 5 hours at 0° C. During this period, the reaction mixture changed from bright red to orange. Immediately upon completion of the reaction, the reaction mixture was carbonated with dry-ice in a dry-box under a nitrogen atmosphere and let stand overnight. The resulting white solid mass was then hydrolyzed with water (3 ml.). After the removal of all volatile components under vacuum, the solid paste was dissolved in water and washed with pentane. The aqueous layer was rendered acidic with dilute hydrochloric acid and extracted with heptane. The heptane extract was dried over sodium sulfate, filtered and concentrated to afford 5.22 g. of oily liquid. Upon measurement of NMR, IR, mass spectra of the product and gas-chromatographic analysis of the corresponding methyl ester obtained by treating the acid-product with diazomethane (gas chromatography on a 3% OV-101, ⅛ inch O.D., 6ft. column with temperature increase at a rate of 8° C./min. from 150° C.), the material was found to be 2-(3-phenoxyphenyl)propionic acid (98% pure) in a yield of 77.4% based on 3-ethylbiphenyl ether.

The spectroscopic data of the product 2-(3-phenoxyphenyl)-propionic acid:

NMR(CDCl$_3$, TMS): $\delta$1.44(d,J=7H$_z$, 3H), 3.68 (q, J=7H$_z$, 1H), 6.73–7.54 (m, 9H).

IR (Neat): 2940, 2595, 1697, 1656, 1480, 1450, 1415, 1243, 1165, 1074, 933, 757 694 cm$^{-1}$.

This agrees exactly with the spectra of a known sample of 2-(3-phenoxyphenyl)propionic acid.

EXAMPLE 2

This experiment was conducted using the same starting materials and the same reaction procedures as used in Example 1, but without anisole. Extraction with ether resulted in the product of 4.83 g. of crude 2-(3-phenoxyphenyl)propionic acid (90% pure) containing 8% 2-(3-ethylphenoxy)benzoic acid and 2% 2-methyl-2-(3-phenoxyphenyl)-malonic acid. Yield 65%.

EXAMPLE 3

To a mixed solvent of dried 1-methylpyrrolidine (6.0 ml.) and triethylamine (10.0 ml.) were added potassium tertiary-butoxide (11.7 g., 104 mmoles), 4.15 ml. 1,4-diethylbenzene (3.60 g., 26.8 mmoles). The flask was flushed with nitrogen, and the reaction mixture was stirred in an ice-water bath for 15 minutes. n-Butyllithium (2.50 M.) (8.0 ml, 20.0 mmoles) was charged dropwise into the flask over a period of 10 minutes. A red suspension developed upon additions of n-butyllithium. The mixture was stirred for 5 hours under ice-water cooling. After completion of the reaction, the reaction mixture was carbonated with 200 ml. of dry-ice inside a dry-box under a nitrogen atmosphere. The resulting white solid mass was then hydrolyzed with water (3 ml.) on the next morning. After removal of all volatile components under vacuum, the solid paste was dissolved in water and washed with pentane. The aqueous layer was acidified with dilute hydrochloric acid and extracted with ether. The combined ether extracts were dried over sodium sulfate, filtered and concentrated to afford 4-ethylphenylpropionic acid (2.76 g., 15.5 moles), corresponding to a yield of 77.5% based on n-butyllithium.

The NMR spectrum of 4-ethylphenylpropionic acid in the product:

NMR (CD$_3$SOCD$_3$, TMS): $\delta$1.16(t, 7H$_z$, 3H), 1.40 d, 7H$_z$, 3H), 2.60(q, 7H$_z$, 2H), 3.69(q, 7H$_z$, 1H), 6.96–7.40 (m, 4H).

EXAMPLE 4

To a dried solvent of 1-methylpyrrolidine (80 ml.) were added potassium tertiary-butoxide (17.5 g., 156 mmoles), 6.40 ml. $\beta$-ethylnaphthalene (6.30 g., 40.4 mmoles) under a nitrogen atmosphere. After stirring for 15 minutes under ice-water cooling, n-butyllithium (2.50 M) (12.0 ml, 30.0 mmoles) was introduced dropwise over a period of about 10 minutes. A greenish blue color developed and the contents began jelling up. Additional 1-methylpyrrolidine (50 ml.) was added to help bring the jell back into solution. The reaction was continued for 5 hours at 0° C. The final color was bluish green. The reaction mixture was then transferred into a dry-box and carbonated with dry-ice (200 ml.) under a nitrogen atmosphere. On the next morning, the white solid mass was hydrolyzed with water (3 ml.). After the removal of the volatile materials under vacuum, the pasty material was dissolved in water, washed with hexane and extracted with ether (3 times). The combined ethereal extracts were dried over sodium sulfate, filtered and concentrated to afford the crude 2-($\beta$-naphthyl)propionic acid crystals (3.43 g.). Upon measurement of NMR spectrum of the product and gas chromatographic determination of the corresponding methyl ester obtained by treating the acid-product with diazomethane (chromatography on a 3% OV-101, ⅛ inch O.D. 6 ft. column with a temperature increase at a rate of 8° C./min. from 150° C.), the isolated crude material was found to be a mixture of 2-($\beta$-naphthyl)propionic acid and 2-methyl-2-($\beta$-naphthyl)malonic acid in a ratio of 94:6. That is, the yield of 2-($\beta$-naphthyl)propionic acid was 53% based on n-butyllithium.

NMR(CD$_3$SOCD$_3$, TMS): $\delta$1.58(d, 7H$_z$, 3H), 3.98(q. 7H$_z$, 1H), 7.30–8.16(m, 7H).

EXAMPLE 5

The reaction was run in the same manner as in Example 3, except that 3.30 ml. of 3-methylanisole (3.20 g., 26.2 mmoles) were used in place of 1,4-diethylbenzene. The same workup afforded 97.3% pure 3-methoxyphenylacetic acid (4.05 g., 26.2 mmoles) corresponding to the yield of 100%, based on 3-methylanisole.

The NMR spectrum of 3-methoxyphenylacetic acid in the product:

NMR(CD$_3$SOCD$_3$, TMS): $\delta$3.56(s, 2H), 3.70(s, 3H), 6.64–7.43(m, 4H).

EXAMPLE 6

The reaction was conducted using the same materials and the same procedures as used in Example 1, but using 4.50 ml. ethylbenzene (3.90 g., 36.8 mmoles) as the starting material in place of the mixture of 3- and 4-ethylbiphenyl ether. The same workup using ether for extraction gave 3.22 g. (21.5 mmoles) of pure 2-phenylpropionic acid. Yield 72% (based on n-butyllithium).

NMR(CD$_3$SOCD$_3$, TMS): $\delta$1.42(d, 7H$_z$, 3H), 3.72 (q, 7H$_z$, 1H), 7.07–7.53 (m, 5H).

EXAMPLE 7

The reaction was run in the same manner as in Example 1, except that the order of addition of ethylbiphenyl ether and n-butyllithium was reversed to preform the complex-aggregate: to a mixed solvent of dried 1-methylpyrrolidine and triethylamine containing potassium tertiary-butoxide and anisole was added n-butyllithium at 0° C. (15 minutes) followed by ethylbiphenyl ether. Then, the reaction mixture was stirred at 0° C. for 4 hours before carbonation. An identical workup afforded 5.24 g. 2-(3-phenoxyphenyl)propionic acid (98% pure) in a yield of 77.7% based on 3-ethylbiphenyl ether.

EXAMPLE 8

The reaction was run in the same manner as in Example 2 without anisole, except that the order of addition of ethylbiphenyl ether and n-butyllithium was reversed to preform the complex-aggregate and that the addition of n-butyllithium was carried out at −20° C. (15 minutes) followed by ethylbiphenyl ether at the same temperature. Then, the reaction mixture was stirred at −20° C. for 1 hour, and at 0° C. for 3 hours before carbonation. The same workup resulted in the product of 5.44 g. of 2-(3-phenoxyphenyl)propionic acid (97% pure) in a yield of 80.0% based on 3-ethylbiphenyl ether.

COMPARATIVE EXAMPLE 1

In this example sodium tertiary-butoxide instead of potassium tertiary-butoxide was used as a complexing agent and the benzyl anion was not formed, i.e. no transmetallation reaction occurred.

To an 80 ml. of 1-methylpyrrolidine solvent were charged sodium tertiary-butoxide (15.0 g., 160 mmoles), an isomeric mixture of 3- and 4-ethylbiphenyl ether (8.00 g., 40.4 mmoles) containing 85% pure 3-ethylbiphenyl ether (6.80 g., 34.3 mmoles) under a nitrogen atmosphere under ice-water cooling with stirring until all sodium tertiary-butoxide dissolved (about 15 minutes). n-Butyllithium (2.50 M) (12.0 ml., 30.0 mmoles) was then added dropwise to the reaction mixture (10 minutes). No red color in the reaction mixture was developed upon complete addition of n-butyllithium. The color of the reaction mixture remained yellow throughout the reaction period of 5 hours under ice-water cooling. The reaction mixture was routinely carbonated and acidified. A normal workup gave 3.08 g. brown sticky product. Upon measurement of NMR spectrum of the product and gas-chromatographic analysis of the corresponding methyl ester obtained by treating the acid-product with diazomethane, the material was found to be a mixture of 3- and 4-ethylphenoxybenzoic acids, and hardly any trace of the desired 2-(3-phenoxyphenyl)propionic acid was detected. That is, the combined yield of 3- and 4-ethylphenoxybenzoic acids was 31.5% based on 3- and 4-ethylbiphenyl ether.

The NMR spectrum of the mixture of 3- and 4-ethylphenoxybenzoic acids:

NMR(CD$_3$SOCD$_3$, TMS): $\delta$1.17(t, 7H$_z$, 3H), 2.62(q, 7H$_z$, 2H) 6.60–7.72(m, 7H), 7.96(dd, 2H$_z$, 8H$_z$, 1H).

COMPARATIVE EXAMPLE 2

A series of experiments were conducted using the same starting material and the same reaction procedures as used in Example 1 and Example 2 with and without anisole, but using 3.50 g., 7.00 g., 10.50 g., 14.00 g., 17.50 g., 21.00 g. of potassium tertiary-butoxide powder corresponding to the potassium tertiary-butoxide: n-butyllithium ratio of 1:1, 2:1, 3:1, 4:1, 5:1 and 6:1 respectively. The yields of 2-(3-phenoxyphenyl)propionic acid versus the potassium tertiary-butoxide/n-butyllithium ratio are expressed in the table below:

| Ratio | % Yield with anisole | % Yield without anisole |
| --- | --- | --- |
| 1:1 | 21 | 21 |
| 2:1 | 29 | 30 |
| 3:1 | 53 | 53 |
| 4:1 | 65 | 60 |
| 5:1 | 76 | 65 |
| 6:1 | 76 | 66 |

At the 1:1 ratio, where there is only sufficient potassium tertiary-butoxide for the exchange reaction with n-butyllithium, the yield is much lower than that obtained using the complex-aggregate of this invention. The use of potassium t-butoxide in excess of a 5:1 ratio is neither beneficial or detrimental.

COMPARATIVE EXAMPLE 3

In this example cyclohexane was used as a reaction medium in which potassium tertiary-butoxide is not soluble resulting in a negligible amount of acid product.

To a 125 mol. of cyclohexane solvent was charged potassium tertiary butoxide (14.0 g., 125 mmoles) under a nitrogen atmosphere under ice-water cooling with stirring. Then, n-butyllithium (2.50 M) (10.0 ml., 25.0 mmoles) was added followed by 9.75 ml. of the isomeric mixture of 3- and 4-ethylbiphenyl ether (9.75 g., 49.2 mmoles). The reaction mixture turned red-orange and the content was sparingly soluble. A routine workup following carbonation and acidification gave only a negligible amount of acid derivatives.

COMPARATIVE EXAMPLE 4

In this example 15.0 wt. % potassium tertiary-amylate solution in cyclohexane (a more soluble potassium tertiary-alkoxide) was used in place of potassium tertiary-butoxide; the reaction proceeded sluggishly resulting in a very low yield of the desired product.

To a 117 ml. of 15.0 wt. % solution of potassium tertiary-amylate in cyclohexane (7.36 g., 111 mmoles) under a nitrogen atmosphere under ice-water cooling was charged 9.75 ml. of an isomeric mixture of 3- and 4-ethylbiphenyl ether (9.75 g., 49.2 mmoles) containing 85% pure 3-ethylbiphenyl ether (8.29 g., 41.9 mmoles) with stirring. Then 10.0 ml. n-butyllithium (2.50 M) (25.0 mmoles) was added dropwise to the reaction mixture (10 minutes). The reaction mixture was carbonated after reaction for 5 hours at 0° C. The standard workup yielded 3.55 g. brown sticky product material which was revealed by $^1$H NMR spectrum to be a mixture of 2-(3-phenoxyphenyl)propionic acid, 2-(3-ethylphenoxy)benzoic acid and 2-methyl-2-(3-phenoxyphenyl)malonic acid at a ratio of 28:68:4. That is, the yield of 2-(3-phenoxyphenyl)propionic acid (fenoprofen) was 16.4% based on n-butyllithium.

COMPARATIVE EXAMPLE 5

In this example tetrahydrofuran was used as a reaction solvent and the n-butyllithium-potassium tertiary-alkoxide complex was found decomposed in this solvent-system.

To a 125 ml. of dry tetrahydrofuran (dried over lithium aluminum hydride) were charged potassium tertiary-butoxide (14.0 g., 125 mmoles), 13.0 ml. of 3- and 4-ethylbiphenyl ether (13.0 g., 65.7 mmoles) in a nitrogen atmosphere at −20° C. in a dry-ice/acetone bath. n-Butyllithium (2.50 M) (12.5 ml., 31.3 mmoles) was added dropwise into the reaction mixture. Each n-butyllithium drop only generated a transient red color and no red color developed upon completion of addition of all the n-butyllithium at this temperature (−20° C.).

I claim:

1. A method of preparing an alkanoic acid of the formula $$Ar-\overset{R^6}{\underset{|}{CH}}-COOH$$

in which $R^6$ is a $C_{1-4}$ alkyl group or a hydrogen atom and Ar is a substituted or unsubstituted aromatic group of the formula

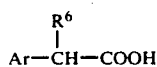

wherein $R^7$ and $R^8$ may be the same or different and each represents a hydrogen atom; an alkyl group; an aryl group; an $OR^9$ group in which $R^9$ represents a hydrogen atom, an alkyl group, an aryl group; or a protected O=C-$R^{10}$ group in which $R^{10}$ represents an alkyl or aryl group; or a group of the formula:

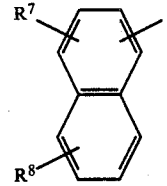

comprising the step of contacting and metallating an alkyl aromatic compound of the formula $$AR-CH_2-R^6$$

with a metallating reagent solution comprising the reaction product of $$Li\ R^1$$

where $R^1$ is a $C_{1-10}$ alkyl group, a lower alkoxyphenyl or dialkoxyphenyl group in which the alkoxy group has 1 to 4 carbon atoms or an aryloxyphenyl group, and between about two and five molar equivalents of $$KOR^2$$

where $R^2$ is a tert-alkyl group having 4 to 7 carbon atoms, in one or more trialkylamines of the formula $$NR^3R^4R^5$$

where $R^3$, $R^4$ and $R^5$ are each a $C_{1-18}$ alkyl group or $R^3$ and $R^4$ form together an α-ω-alkylene group containing from 1 to 8 carbon atoms.

2. A method according claim 1 wherein the reaction is carried out at a temperature between about −25° C. and +25° C.

3. A method according to claim 1 in which an aryl ether of the formula $$Ar-O-R^{11}$$

in which $R^{11}$ is a $C_{1-4}$ alkyl group or an Ar group and Ar is a substituted or unsubstituted aromatic group of the formula

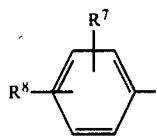

wherein $R^7$ and $R^8$ may be the same or different and each represents a hydrogen atom, an alkyl group, an aryl group, an $OR^9$ group in which $R^9$ represents an alkyl group or an aryl group; or a group of the formula:

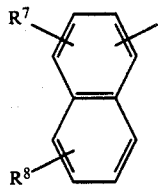

is present in the reaction mixture in an amount about equimolar to the alkylaromatic compound.

4. A method according to claim 3 in which the aryl ether is anisole.

5. A method according to claim 1 in which Ar is 3-phenoxyphenyl, 4-isobutylphenyl, 6-methoxynaphth-2-yl, 4-biphenyl, 3-benzoylphenyl or phenyl and $R^6$ is methyl.

6. A method according to claim 5 in which the reagent comprises the reaction mixture of potassium tert-butoxide or potassium tert-amylate and n-butyllithium or tert-butyllithium in a trialkylamine solvent.

* * * * *